United States Patent [19]

Krbechek

[11] 4,251,450

[45] Feb. 17, 1981

[54] NITROGEN TRANSHALOGENATION PROCESS

[75] Inventor: Leroy O. Krbechek, Minneapolis, Minn.

[73] Assignee: Henkel Corporation, Minneapolis, Minn.

[21] Appl. No.: 122,398

[22] Filed: Feb. 19, 1980

[51] Int. Cl.³ .................................................. C07J 9/00
[52] U.S. Cl. ................................ 260/397.1; 260/397.3
[58] Field of Search ........................... 260/397.1, 397.3;
/Steroids MS File

[56] References Cited

U.S. PATENT DOCUMENTS 3,149,102  9/1964  Georgian et al. ................. 260/239.5
3,591,611  7/1971  Arth et al. ......................... 260/397.3

OTHER PUBLICATIONS

Julian et al., "JACS" (1948) No. 3, pp. 887–892.

*Primary Examiner*—Elbert L. Roberts
*Attorney, Agent, or Firm*—Forrest L. Collins; Patrick J. Span

[57] ABSTRACT

The present invention describes the transhalogenation of amido compounds to obtain the corresponding N-haloamide through the use of an N-haloimide.

28 Claims, No Drawings

NITROGEN TRANSHALOGENATION PROCESS

BACKGROUND OF THE INVENTION

1. Field of the Invention

The present invention relates to the transfer of halogen atoms from one nitrogen-containing compound to another nitrogen-containing compound.

2. Description of the Art

It is known that progesterone and progesterone-like compounds can be made through a variety of routes. In the present invention, 20-carboxamido compounds are utilized to form progesterone and its analogs. One route utilizing an acid functionality on the steroid side chain is reported in an article entitled, "The Conversion of Hyodesoxycholic Acid to Progesterone", by Bharucha, et al, as reported in the *Canadian Journal of Chemistry*, Vol. 34, 1956 at page 982–990. The Bharucha, et al, route also utilizes N-bromosuccinimide as one of the reactants in this process. Another route utilizing an acid, this time a 20-carboxy acid of a steroid to obtain progesterone via the Oppenauer oxidation is reported by Wieland, et al, in Helvetica Chimica Acta, Vol. XXXII, Part VI (1949), No. 255 at page 1922–1933. Wieland again with his coauthor Mischler at Helvetica Chimica Acta, Vol. XXXII, Part V (1949), No. 233 at pages 1764–1769 again reports a method for obtaining progesterone through a complicated route utilizing a 20-carboxy steroid compound.

Julian, et al, in an article entitled, "Delta 20-pregnenes from Bisnor-Steroid Acids", as reported in JACS at Vol. LXX, published 1948, No. 3, at pages 887–892, reports that 20-carboxy steroids may be converted to useful steroids. In another article published in Helvetica Chimica Acta at Vol. XXXII, Part V (1949), No. 232 at pages 1758–1763, Meystre, et al, report that 20-carboxy steroid compounds may be converted to the corresponding chloroamine and thereafter, through a multistep reaction, progesterone may be obtained. U.S. Pat. No. 3,519,658 issued to Adam, et al, July 7, 1970 discusses the use of N-chlorosuccinimide with steroids.

Useful steroids having a 20-carboxyl functionality are described in European Patent application No. 4-913 published Oct. 31, 1979. An additional useful product obtained therein is 3-oxo-pregna-1,4,17(20)-triene-20-carboxylic acid. More useful acids are described in U.S. Pat. No. 3,994,933 issued to Jiu, et al, Nov. 30, 1976.

To the extent that each of the foregoing references is applicable to the present invention, it is herein specifically incorporated by reference.

Throughout the specification and claims the percentages and ratios are given by weight and temperatures are in degrees Celsius unless otherwise indicated.

SUMMARY OF THE INVENTION

The present invention describes a process for the transhalogenation of an amido compound to form the corresponding N-haloamide comprising contacting the amido compound with an N-haloimide.

The invention also discloses the formation of N-haloamides of steroids as hereinafter discussed.

DETAILED DESCRIPTION OF THE INVENTION

The present invention as previously noted in its broadest aspect relates to the transhalogenation of an amido compound to form the corresponding N-haloamide through reacting the amido compound with an N-haloimide. Thus, materials such as stearyl amide, benzylamide, or phenylacetamide may be contacted with the N-haloimide, whereupon the N-haloimide transfers the halogen to the amide.

The most practical use of the present invention, however, involves the conversion of steroidal amides to their corresponding carbamates by obtaining as an intermediate product the corresponding N-haloamide of the steroidal amide, Shown below in (A) is 3-oxo-pregna-1,4-diene-20-carboxylic acid. Also shown at (B) is 3-oxo-pregn-4-ene-20-carboxylic acid.

Shown at (C) is 3-oxo-pregna-1,4,17(20)-triene-20-carboxylic acid. At (D) the basic structure shown is that of 3-oxo-pregna-4,17(20)-diene-20-carboxylic acid.

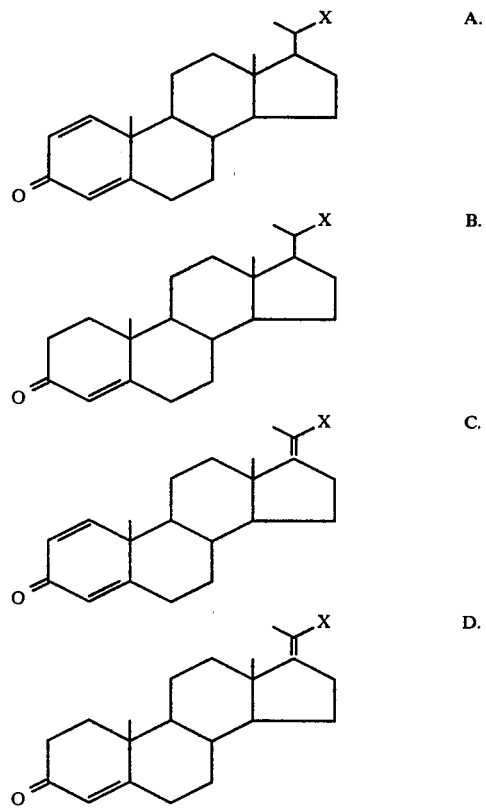

Where X is COOH, the acid is shown. The acid may be converted to the acid halide (chloride) where X is COCl which upon ammonical treatment forms the amide X being $CONH_2$. The present invention generates the haloamide (here bromine) with X being CONHBr.

These carboxylic acid amides are first obtained from the corresponding 20-carboxylic acid which may be obtained as suggested in Jiu, U.S. Pat. No. 3,994,993 issued Nov. 30, 1976 herein incorporated by reference. The remaining starting materials in the present invention may be obtained from the technology embodied in European application No. 4-913 published Oct. 31, 1979 herein incorporated by reference.

The formation of the N-haloamide as previously noted requires an N-haloimide. Preferably the halogen on the N-haloimide is bromine then chlorine, although fluorine and iodine may also be utilized. The preferred N-haloimides are a member selected from the group consisting of N-bromosuccinimide and N-bromophthalimide.

The reaction may be conducted in the presence or absence of a solvent and some selection of solvent is required if it is desired to directly obtain the N-haloamide directly. That is, in the most preferred aspect of the present invention, an alcohol such as methanol is utilized in the reaction mixture and the N-haloamide is converted through the use of a strong base preferably such as sodium methoxide and sodium or potassium hydroxide directly to the corresponding carbamate. However, where an aprotic solvent is employed, it is possible to obtain the haloamide product directly. It should be noted it is not convenient to run the present reaction in the absence of any solvent due to the high viscosity of the components of the reaction. It is beneficial to use a mixed solvent system of an alcohol and a halogenated hydrocarbon preferably at a respective weight ratio of from about 15:1 to about 1:10. Of course, sufficient alcohol must be included when the carbamate is to be formed. The halogenated hydrocarbon is preferably methylene chloride although ethylene dichloride may be employed. The alcohols include methanol, ethanol, n-propanol, benzyl alcohol, 2-propanol, n-butanol, 2-butanol, t-butanol, and the 2-alkoxy alkanols (Cellosolves) such as 2-methoxyethanol and mixtures thereof.

It is highly desirable when conducting the reaction to the present invention that the water content be limited. Surprisingly, water up to 5%, preferably not more than 2.5% of the weight of the reactants may be present without difficulty. It is desirable to run the reaction under a nitrogen atmosphere and also to purge the reaction vessel for a period of several minutes prior to the reaction. If the solvent is to be dried, calcium hydride is recommended. Where the carbamate is desired, a urethane catalyst such as dibutyl tin dilaurate may be included.

The reaction itself as noted is conducted under an inert atmosphere thus requiring a small amount of pressure to maintain the inert atmosphere. The temperature at which the reaction is conducted may be anywhere from 0°–95° C. depending upon the quantity of reactants employed and the difficulty in controlling the reaction in either elevated or depressed temperatures. The amount of N-haloimide employed is the equivalent amount required although excess amounts from 1.1 to 5.0 equivalents preferably from 1.2 to 3.0 equivalents may be used to ensure substantially complete N-haloamide formation. It has been found convenient to add a reducing agent after the N-haloamide has been formed. Sodium thiosulfate may be used for this purpose. The excess base may be neutralized using a Lewis acid such as acetic acid.

The compounds which are obtained through the specification and examples include the esters of the foregoing monohydric alcohols and the N-(halo) steroids of a 20-carboxylic acid amide particularly the chloro and bromo derivatives. The present invention also describes the N-bromo- 3-oxo-pregna-1,4-diene-20-carboxylic acid amide; N-bromo-3-oxo-pregn-4-ene-20-carboxylic acid amide; N-bromo-3-oxo-pregna-1,4,17(20)-triene -20-carboxylic acid amide; and N-bromo-3-oxo-pregna-4,17(20)-diene-20-carboxylic acid amide.

EXAMPLE I

One mole of alpha-benzamide is placed in a sealed reaction flask which has previously been purged with nitrogen. The reaction flask is again purged with nitrogen and this procedure is conducted two more times. The flask also contains sodium methoxide, methylene chloride, and methanol. One equivalent of N-bromosuccinimide is then added and the reaction mixture is controlled at 0° C. under the nitrogen atmosphere for approximately 45 minutes. Conveniently, of course, a slight excess over this amount can be used but some care should be taken not to displace both hydrogen atoms of the amide.

The excess base is then treated with acetic acid to accomplish neutralization. The reaction is substantially complete and the corresponding N-haloamide is found in the reaction mixture. The N-haloamide may then be separated from the reaction mixture.

The preceeding reaction experiment is then repeated utilizing N-bromophthalimide.

EXAMPLE II

The preceeding reaction is run separately on 3-oxopregna-1,4-diene-20-carboxylic acid amide, then on 3-oxo-pregn-4-ene-20-carboxylic acid amide, then on 3-oxo-pregna-1,4,17(20)-triene-20-carboxylic acid amide, and on 3-oxo-pregna-4,17(20)-diene-20-carboxylic acid amide.

Each of the foregoing are run utilizing N-bromosuccinimide; secondly utilizing N-bromophthalimide; and finally using N-chlorosuccinimide. Substantial yields of the corresponding N-haloamide are obtained through the reaction mixture in a high degree of purity.

The N-(halo) amide obtained may be converted to the carbamate by use of the foregoing monohydric alcohols and base.

EXAMPLE III

In this example, 3-oxo-pregn-4-ene-20-carboxylic acid amide is converted through the corresponding N-haloamide to the 3-oxo-pregn-4-ene-20methyl carbamate. In this reaction 1 kg. of the amide is introduced into 4.5 ls. of methanol. The methanol had previously been dried with calcium hydride. Also introduced into the reaction mixture are 375 gs. of sodium methoxide. The reaction mixture is then warmed to 45° C. Six hundred grams of commercially obtained N-bromosuccinimide is then added to the reaction mixture which is maintained at 45° C. under a nitrogen atmosphere. The reaction mixture is stirred for a period of approximately 45 minutes while maintaining the nitrogen atmosphere.

Following the above treatment, the solution was acidified with 2 liters of glacial acetic acid. The residue which remains following solvent removal at reduced pressure is then dissolved in methylene chloride and washed excessively with water, sodium thiosulfate, and water.

The methylene chloride is then removed at reduced pressure and 1,200 gs. of product is obtained. This product analyzed at greater than 80% of the corresponding methyl carbamate. A small amount of residual amide is found in the reaction product.

The reaction may be slightly improved by utilizing a urethane catalyst to obtain a higher yield of the methyl carbamate. Such a urethane catalyst is dibutyl tin dilaurate.

Substantially similar results are obtained in the above reaction when utilizing N-bromophthalimide. Substantially similar results are also obtained when utilizing the corresponding chloro derivatives of the imides.

What is claimed is:

1. A process for the transhalogenation of an amido compound to form the corresponding N-haloamide comprising contacting the amido compound with an N-haloimide.

2. The process of claim 1 wherein the N-haloimide is selected from the group consisting of N-bromosuccinimide and N-bromophthalimide and mixtures thereof.

3. The process of claim 2 wherein the N-haloimide is N-bromosuccinimide.

4. The process of claim 2 wherein the N-haloimide is N-bromophthalimide.

5. The process of claim 1 comprising the additional step of reacting the N-haloamide with a strong base.

6. The process of claim 5 wherein the base is selected from the group consisting of sodium hydroxide, potassium hydroxide and sodium methoxide, and mixtures thereof.

7. The process of claim 6 wherein the corresponding carbamate is formed with a monohydric alcohol.

8. The process of claim 7 wherein the alcohol is selected from the group consisting of methanol, ethanol, 1-propanol, 2-propanol, n-butanol, 2-butanol, t-butanol, 2-alkoxy alkanols, and benzyl alcohol and mixtures thereof.

9. The process of claim 8 wherein the alcohol is methanol.

10. The process of claim 1 which is conducted in an inert atmosphere.

11. The process of claim 1 which is conducted in a solvent system consisting essentially of methanol and methylene chloride.

12. The process of claim 7 wherein the mixture is additionally treated by acidification.

13. The process of claim 12 wherein the acidification is done with acetic acid.

14. The process of claim 12 wherein the reaction mixture is treated with a reducing agent.

15. The process of claim 1 wherein the amido compound is alpha-benzamide.

16. The process of claim 1 wherein the amido compound is a steroid.

17. The process of claim 16 wherein the steroid is a member selected from the group consisting of 3-oxo-pregna-1,4-diene-20-carboxylic acid amide; 3-oxo-pregn-4-ene-20-carboxylic acid amide; 3-oxo-pregna-1,4,17(20)-triene-20-carboxylic acid amide; and 3-oxo-pregna-4,17(20)-diene-20-carboxylic acid amide and mixtures thereof.

18. The process of claim 16 wherein the N-haloimide is N-bromosuccinimide.

19. The process of claim 1 which is conducted at from about 10° Celsius to about 60° Celsius.

20. The process of claim 17 wherein the steroid is obtained as the methyl carbamate.

21. The process of claim 20 wherein a urethane forming catalyst is present.

22. A compound selected from the group consisting of the N-(halo) steroid derivatives of a 20-carboxylic acid amide.

23. The compound of claim 22 which is the N-chloro or N-bromo derivative.

24. N-bromo-3-oxo-pregna-1,4-diene-20-carboxylic acid amide.

25. N-bromo-3-oxo-pregn-4-ene-20-carboxylic acid amide.

26. N-bromo-3-oxo-pregna-1,4,17(20)-triene-20-carboxylic acid amide.

27. N-bromo-3-oxo-pregna-4,17(20)-diene-20-carboxylic acid amide.

28. The process of claim 8 wherein the alcohol is t-butanol.

* * * * *